US00PP27538P3

(12) United States Plant Patent
Layt

(10) Patent No.: US PP27,538 P3
(45) Date of Patent: Jan. 10, 2017

(54) ***STENOTAPHRUM SECUNDATUM* PLANT NAMED 'PAL42'**

(50) Latin Name: *Stenotaphrum secundatum*
Varietal Denomination: PAL42

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 0 days.

(21) Appl. No.: 14/757,009

(22) Filed: Nov. 6, 2015

(65) Prior Publication Data

US 2016/0135351 P1 May 12, 2016

Related U.S. Application Data

(60) Provisional application No. 62/078,675, filed on Nov. 12, 2014.

(51) Int. Cl.
*A01H 5/12* (2006.01)

(52) U.S. Cl.
USPC ..... Plt./392

(58) Field of Classification Search
USPC ..... Plt./392
See application file for complete search history.

*Primary Examiner* — Annette Para
(74) *Attorney, Agent, or Firm* — Samuel R. McCoy, Jr.

(57) ABSTRACT

A new and distinct turf grass cultivar of *Stenotaphrum secundatum* plant named 'PAL42', characterized by the combination of greater internodal spacing of the stolons, very long stolons, and a very fast growth rate; characteristics which translate to a highly aesthetic turf grass that exhibits improved environmental tolerances and lower production and maintenance input costs.

1 Drawing Sheet

Latin name of genus and species of plant claimed: The Latin name of the genus and species of the novel variety disclosed herein is *Stenotaphrum secundatum.*

Variety denomination: The novel variety of *Stenotaphrum secundatum* disclosed herein has been given the variety denomination 'PAL42'.

BACKGROUND OF THE INVENTION

The present invention relates to a new and distinct variety of *Stenotaphrum secundatum,* commonly identified as St. Augustine grass, which has been given the variety denomination of 'PAL42'. Its market class is PLT/392 and is commonly classified by the ornamental horticulture industry as a warm season turf grass.

Parentage: The new *Stenotaphrum secundatum* cultivar is a seedling selection resulting from an open-pollination breeding program conducted from 2004 to 2012 at a commercial plant breeding facility in Clarendon, NSW Australia. 'Pal42' is a seedling selection from said breeding program which resulted from the open pollination of proprietary accessions developed from progeny of *Stenotaphrum secundatum* 'SS100' (U.S. Pat. No. 9,395). Beginning in 2004 and continuing in 2005, said accessions were planted into community propagation trays and allowed to cross pollinate. In 2006, the resulting seed was harvested from said propagation trays and was subsequently sown which resulted in approximately one hundred progeny that exhibited improved plant vigor. These seedlings were potted into 140 mm nursery pots and grown on for evaluation. In 2007, the number of candidates was reduced to thirty-two progeny that exhibited a combination of superior vigor and turf quality when compared to other candidates in the breeding program. The number of candidate progeny was further reduced to five later in that same year. The following year, all but two candidate progeny were eliminated from the breeding program. At this time, both candidates were asexually propagated to expand the sample size of the breeding trials. In the summer of 2012, one of the remaining two candidate progeny was selected for its fast growth rate, greater internodal spacing of the stolons, improved disease resistance, and improved frost tolerance.

Asexual Reproduction: 'PAL42' was first asexually propagated by division of rhizomes in 2008 in Clarendon, NSW Australia. 'PAL42' has since been further asexually propagated by means of cutting and division of rhizomes. The distinctive characteristics of the variety have remained stable and true to type through successive cycles of asexual propagation.

SUMMARY OF THE INVENTION

A new and distinct turf grass cultivar of *Stenotaphrum secundatum* plant named 'PAL42', characterized by the combination of greater internodal spacing of the stolons, very long stolons, and a very fast growth rate; characteristics which translate to a highly aesthetic turf grass that exhibits improved environmental tolerances and lower production and maintenance input costs.

BRIEF DESCRIPTION OF THE PHOTOGRAPHS

The FIGURE illustrates, as nearly true as it is reasonably possible to make the same in color illustrations of this type, typical foliage and growth characteristics of the new cultivar. Colors in the photographs differ slightly from the color values cited in the detailed description, which accurately describes the colors of 'PAL42'.

DETAILED BOTANICAL DESCRIPTION

The following is a detailed botanical description of a new and distinct variety of a *Stenotaphrum secundatum* turf grass plant known as 'PAL42'. Plant observations were made on plants grown in Awendaw, S.C., USA. Unless indicated otherwise, the descriptions disclosed herein are based upon observations made in November 2014 of mature and unpruned 'PAL42' plants, approximately 15 months old, grown in 3 gallon nursery pots filled with soilless potting media, maintained with granular slow release fertilizer in an outdoor growing area in filtered sunlight and regularly watered with overhead irrigation. No pest and disease measures were taken.

Those skilled in the art will appreciate that certain characteristics will vary with older or, conversely, younger plants. 'PAL42' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on *The Royal Horticultural Society Color Chart*, of The Royal Horticultural Society, London, 1986 edition.

Plant description:

*Growth habit.*—A long-lived, stoloniferous perennial grass with an upright to decumbent growth habit forming a dense sward of foliage on the ground surface.

*Height.*—Measured from soil level, the sward of 'PAL42' exhibits a general approximate height of 15 cm with the tallest blades reaching 21 cm above soil level, as measured.

*Width.*—Indeterminate.

*Growth rate.*—Highly vigorous.

*Bloom period.*—Spring through fall.

*Hardiness.*—USDA Zone 7 to 11.

*Environmental tolerances.*—Prefers to be grown in full sun but will tolerate partial shade. Relatively drought and heat tolerant once established. Tolerates a wide range of soil types from sandy loam to loamy clay.

*Pest and disease susceptibility or resistance.*—In common with the species, none of note.

*Propagation.*—Propagation is accomplished through division of rhizomes. Typical time to develop roots is approximately 2 to 4 weeks and an average crop time to produce an initial mature and marketable stand of turf grass sod is approximately 6 to 9 months. Precise timing varies depending on fertilizer and water inputs as well as geographical location.

Roots:

*General description.*—Root system consists of numerous coarse and fibrous feeder roots.

*Number of rhizomes.*—Absent.

Foliage:

*Attachment.*—Cauline.

*Length of blade.*—Longest observed measuring 160 mm.

*Width of blade.*—8.5 mm at widest point.

*Shape of blade.*—Linear.

*Leaf shape; apex.*—Rounded.

*Leaf aspect.*—Concave.

*Margin.*—Serrulate.

*Texture of top surface.*—Glabrous.

*Texture of bottom surface.*—Glabrous.

*Leaf color (adaxial surface).*—Juvenile: Green (RHS 137C); mature: Green (RHS 137C).

*Leaf color (abaxial surface).*—Juvenile: Yellow-green (RHS 147B); mature: Yellow-green (RHS 147B).

*Venation.*—Type: Parallel.

*Venation color.*—Indistinguishable.

*Leaf sheath.*—Split with margins touching but not overlapping and approximately 53 mm long on the longest measured leaf blade; glabrous. Color approximates to Green (RHS 137C).

*Collar.*—Broad; extending from leaf margin to leaf margin. Length is approximately 3 mm long, from the sheath to the leaf blade. Color approximates to Yellow-green (RHS 144C).

*Ligule.*—Hairy; comprised of a short line of hairs, approximately 2 mm long.

*Auricle.*—Absent.

*Culm.*—Absent.

Flower:

*Natural flowering season.*—Spring to fall; in Northern hemisphere, April to November.

*Inflorescence type and habit.*—A flattened, spike-like corky raceme with florets embedded in hollows and occurring only on one side of the inflorescence.

*Total inflorescence size.*—50 to 70 mm long by 3.5 mm wide.

*Inflorescence color.*—Yellow-green (RHS 146A).

*Quantity of inflorescences.*—varies by time of year; sparse, as observed.

*Quantity of florets per spike.*—18 to 22 florets.

*Color of florets.*—The lemma and palea are Yellow-Green (RHS 146C).

*Dimensions of florets.*—Approximately 4.5 mm long and less than 1.5 mm wide.

Reproductive organs:

*Stamens.*—Not observed to date.

*Style.*—Not observed to date.

*Stigma.*—Featherlike; length is approximately 1 mm; wide is minute; color is White 155A.

*Ovary.*—Not observed to date.

Seeds and fruits: Not observed to date.

Comparison of 'PAL42' with other varieties of *Stenotaphrum secundatum*

Plants of the new cultivar 'PAL42' are similar to *Stenotaphrum secundatum* 'SS-100', in many horticultural characteristics. Both 'SS-100' and 'Pal42' possess dark green foliage, white stigmas, and exhibit improved cold and frost tolerance. However, 'Pal42' exhibits longer stolons, greater internodal spacing of stolons, longer leaf blades and a faster rate of growth. In side by side field trials conducted in Clarendon, NSW, Australia, the mean stolon internode length of 'Pal42' was 57.69 mm, whereas the mean stolon internode length of 'SS-100' was 49.75 mm. Said longer internodes translates to significantly longer stolons and a faster growth rate in 'Pal42', compared to that of 'SS-100'. In the same trial, mean leaf blade length of 'Pal42' was 40.42 mm where the mean leaf blade length of 'SS-100' was 28.82 mm.

That which is claimed is:

1. A new and distinct variety of *Stenotaphrum secundatum* plant named 'PAL42', substantially as described and illustrated herein.

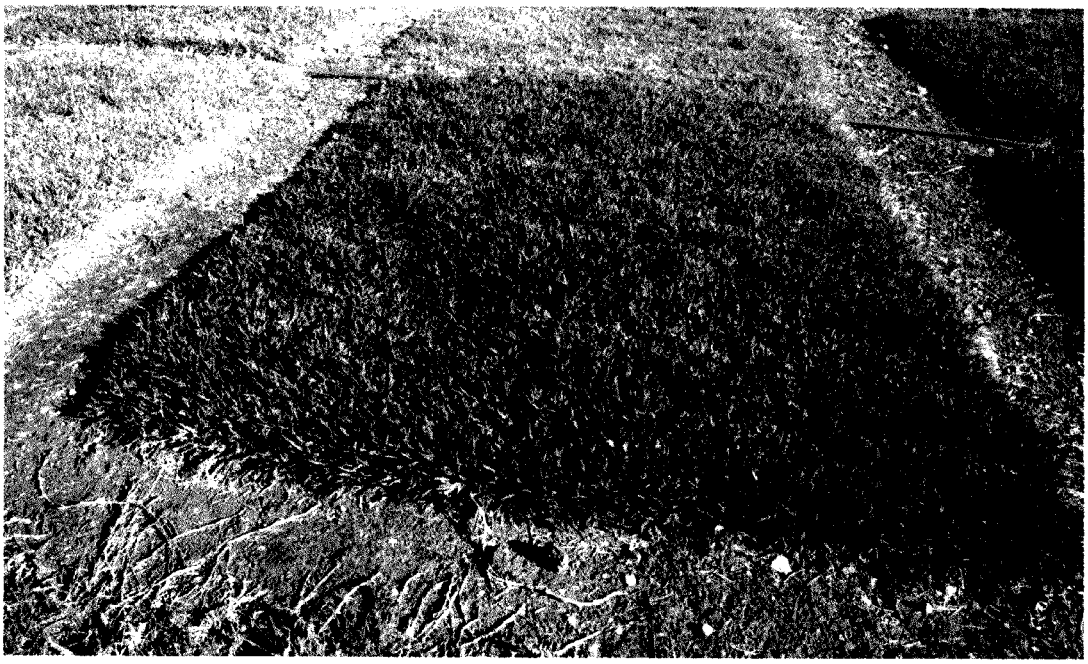

* * * * *